United States Patent
Ehben et al.

(10) Patent No.: US 7,447,538 B2
(45) Date of Patent: Nov. 4, 2008

(54) METHOD AND APPARATUS FOR DISPLAYING A TISSUE CONTAINING A FLUORESCENT DYE

(75) Inventors: Thomas Ehben, Weisendorf (DE); Sebastian Schmidt, Erlangen (DE); Wolfgang Strob, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 163 days.

(21) Appl. No.: 11/525,905

(22) Filed: Sep. 25, 2006

(65) Prior Publication Data

US 2007/0083124 A1    Apr. 12, 2007

(30) Foreign Application Priority Data

Sep. 26, 2005    (DE)    ........................ 10 2005 045 961

(51) Int. Cl.
    *A61B 6/00*    (2006.01)
(52) U.S. Cl. ........................ 600/476; 600/431
(58) Field of Classification Search ................ 600/473, 600/476, 477, 478, 178, 431, 160; 250/461.1; 348/473; 358/98
    See application file for complete search history.

(56) References Cited

U.S. PATENT DOCUMENTS

| | | | |
|---|---|---|---|
| 5,016,173 A | 5/1991 | Kenet et al. | |
| 5,936,728 A | 8/1999 | Bouzid | |
| 5,984,474 A | 11/1999 | Schweitzer et al. | |
| 6,061,591 A * | 5/2000 | Freitag et al. | ............... 600/476 |
| 6,371,615 B1 | 4/2002 | Schweitzer et al. | |
| 6,748,259 B1 * | 6/2004 | Benaron et al. | ............. 600/476 |
| 2005/0179892 A1 | 8/2005 | Gerstner et al. | |

FOREIGN PATENT DOCUMENTS

| | | |
|---|---|---|
| DE | 197 22 790 A1 | 12/1998 |
| DE | 199 16 773 A1 | 10/1999 |
| DE | 199 20 158 A1 | 11/2000 |
| DE | 102 22 779 A1 | 3/2004 |
| DE | 10 2004 006 960 A1 | 8/2005 |
| WO | WO 00/06980 | 2/2000 |

OTHER PUBLICATIONS

German Office Action for corresponding case 10 2005 045 961.7-52.

* cited by examiner

*Primary Examiner*—Eric F Winkur
*Assistant Examiner*—Lawrence N Laryea
(74) *Attorney, Agent, or Firm*—Harness, Dickey & Pierce, P.L.C.

(57) ABSTRACT

A method is disclosed for displaying a tissue containing a fluorescent dye at least in sections. In order to reduce interference signals, it is proposed to record a first fluorescent image during an illumination phase, and a second fluorescent image during a dark phase, and to correct the first fluorescent image by subtracting the second fluorescent image and to process it subsequently to form an overall image.

15 Claims, 2 Drawing Sheets

METHOD AND APPARATUS FOR DISPLAYING A TISSUE CONTAINING A FLUORESCENT DYE

PRIORITY STATEMENT

The present application hereby claims priority under 35 U.S.C. §119 on German patent application number DE 10 2005 045 961.7 filed Sep. 26, 2005, the entire contents of which is hereby incorporated herein by reference.

FIELD

The invention generally relates to a method and/or an apparatus for displaying a tissue containing a fluorescent dye at least in sections.

BACKGROUND

During the surgical removal of a tumor, the problem arises that healthy tissue frequently cannot be distinguished with the naked eye from a tissue affected by a tumor. In order to provide a remedy here, the patient is administered before the operation with a fluorescent dye that is specifically enriched in the tumor. During the operation, the exposed tissue is illuminated with a light in the near infrared region that is suitable for exciting the fluorescent dye. The tissue is recorded with the aid of an image acquisition device that has an optical unit for separating a fluorescent image generated by the fluorescent light, and a native tissue image formed by the ambient light. The recorded fluorescent images and the tissue images are superimposed by way of an image processing device, the tumorous tissue being labeled in the superimposed image by way of, for example, a false color display.

The fluorescent light emitted by the fluorescent dye has a substantially lower intensity by comparison with the ambient light. The fluorescent image must be highly intensified for the purpose of generating images. The problem arises here that the ambient light also includes spectral fractions that correspond to the fluorescent light emitted by the fluorescent dye. These interfering spectral fractions are also intensified during the generation of images and falsify the fluorescent images.

In order to counteract this disadvantage, an attempt is made according to the known systems, to raise the intensity of the fluorescent light emitted by the fluorescent dye. Use is made to this end of a strong exciting light source that includes LEDs for generating light in the near infrared region. The LEDs are operated in a pulsed or clocked fashion in order to attain a particularly high power. It is true that success is thereby achieved in reducing the influence of the interference signal in the generation of images. However, the generation of as exact a fluorescent image as possible entails the aim of further reducing the interference signal or completely suppressing it.

SUMMARY

At least one embodiment of the invention includes a method and/or an apparatus, with the aid of which a fluorescent light emitted by a fluorescent dye can be identified, for example as exactly as possible.

According to at least one embodiment of the invention, a method is provided for displaying a tissue containing a fluorescent dye, at least in sections, the method comprising:

a) illuminating the tissue with a first light that is suitable for exciting the fluorescent dye and has a clock frequency given by a periodic sequence of illumination phases and dark phases, b) separately acquiring first fluorescent images generated during the illumination phases by the excitation of the fluorescent dye, and second fluorescent images generated during the dark phases by an illumination of the tissue with a second light, c) correcting the first fluorescent images by subtracting second fluorescent images corresponding thereto, and d) generating overall images by superimposing on the corrected first fluorescent images corresponding native tissue images which reproduce a tissue surface.

Owing to the separate recording of first fluorescent images recorded with the aid of a first light or exciting light, and of second fluorescent images recorded with the aid of the second light or ambient light, it is possible to subtract the interfering fluorescent fractions contained in the second light. The appropriately corrected first fluorescent images are particularly exact. It is thereby possible to produce a particularly exact overall image of the tissue by virtue of the fact that exactly those fractions of the tissue that are affected by a tumor can be labeled by superimposing the tissue image on the first fluorescent image.

For the purpose of correction, "corresponding" second fluorescent images are used in relation to the first fluorescent images. For the purpose of superimposition, tissue images "corresponding" to the corrected first fluorescent images are used. Within the meaning of the present invention, the term "corresponding" images is understood as images which are such that have been acquired simultaneously or virtually simultaneously and from the same or a similar perspective. It is preferred to make use for corrective purposes of second fluorescent images that have been recorded during the dark phase immediately preceding or following the illumination phase. Likewise, the corrected first fluorescent images are superimposed on tissue images which are such that they have been acquired at the same, or virtually the same time with the first fluorescent images.

According to an advantageous refinement of at least one embodiment, it is provided that the overall image is reproduced with a display frequency. The clock frequency is advantageously an integral multiple, preferably twice the display frequency. The display frequency can be 10 to 60 Hz, preferably 20 Hz. The excitation frequency is thus expediently 40 Hz in the case of a display frequency of 20 Hz.

According to an advantageous further refinement of at least one embodiment of the invention, a number of second fluorescent images are acquired in a fashion following one another temporally during the dark phase. It is thereby possible to resolve a persistence of a fluorescence emission for each illumination phase. The persistence is specific to a fluorescence emission center that generates the fluorescence emission. Different fluorescence emission centers can thereby be detected. The different fluorescence emission centers can be, for example, different fluorescent dyes or else natural fluorescence emission centers. It is thereby possible, for example, to acquire interference signals caused by natural fluorescence emission centers, and thus to carry out a further correction of the first fluorescent images.

To this end, according to a further refinement of at least one embodiment of the invention it is possible for the purpose of producing a second fluorescent image for at least one late fluorescent image acquired during a prescribed late time interval of the dark phase to be subtracted from at least one early fluorescent image acquired in relation to a prescribed early time interval. The proposed correction is based on the finding that, in particular, natural fluorescence emission centers generate a fluorescent light of long persistence.

According to a further advantageous refinement of at least one embodiment, the first fluorescent image is displayed in the overall image by way of a false color. The surgeon can thereby distinguish with particular ease the tumor that is to be removed from the surrounding healthy tissue.

According to a further refinement of at least one embodiment, infrared light, in particular infrared light in the near infrared region, is used as first light. What is involved here is light of a wavelength, in particular, of more than 700 nm, preferably more than 750 nm. The second light can, by contrast, comprise the wavelengths of visible light, that is to say in the range from 350 to 750 nm.

Furthermore, according to at least one embodiment of the invention an apparatus is proposed for the purpose of displaying a tissue containing a fluorescent dye, at least in sections and which comprises:

- an illumination device for illuminating the tissue with a first light that is suitable for exciting the fluorescent dye and has a clock frequency given by a periodic sequence of illumination phases, and dark phases,
- an acquisition device for separately acquiring first fluorescent images generated during the illumination phases by the excitation of the fluorescent dye, and second fluorescent images generated during the dark phases by an illumination of the tissue with a second light,
- a correction device for correcting the first fluorescent images by subtracting second fluorescent images corresponding thereto, and
- an image generating device for generating overall images by superimposing on the corrected first fluorescent images corresponding native tissue images which reproduce a tissue surface.

The proposed apparatus can be used for continuous generation of overall images that enable a tumor to be exactly distinguished from a healthy tissue. In particular, spectral components of the fluorescent light emitted by the fluorescent dye that are contained in the second light or ambient light can be taken into account in correcting the first fluorescent images. The corrected first fluorescent images are particularly exact.

Advantageous refinements of the apparatus follow from the features already described in relation to the method and which can be transferred mutatis mutandis to the apparatus.

BRIEF DESCRIPTION OF THE DRAWINGS

An example embodiment of the invention is explained below in more detail with the aid of the drawings, in which.

DETAILED DESCRIPTION OF THE EXAMPLE EMBODIMENTS

Figure 1:
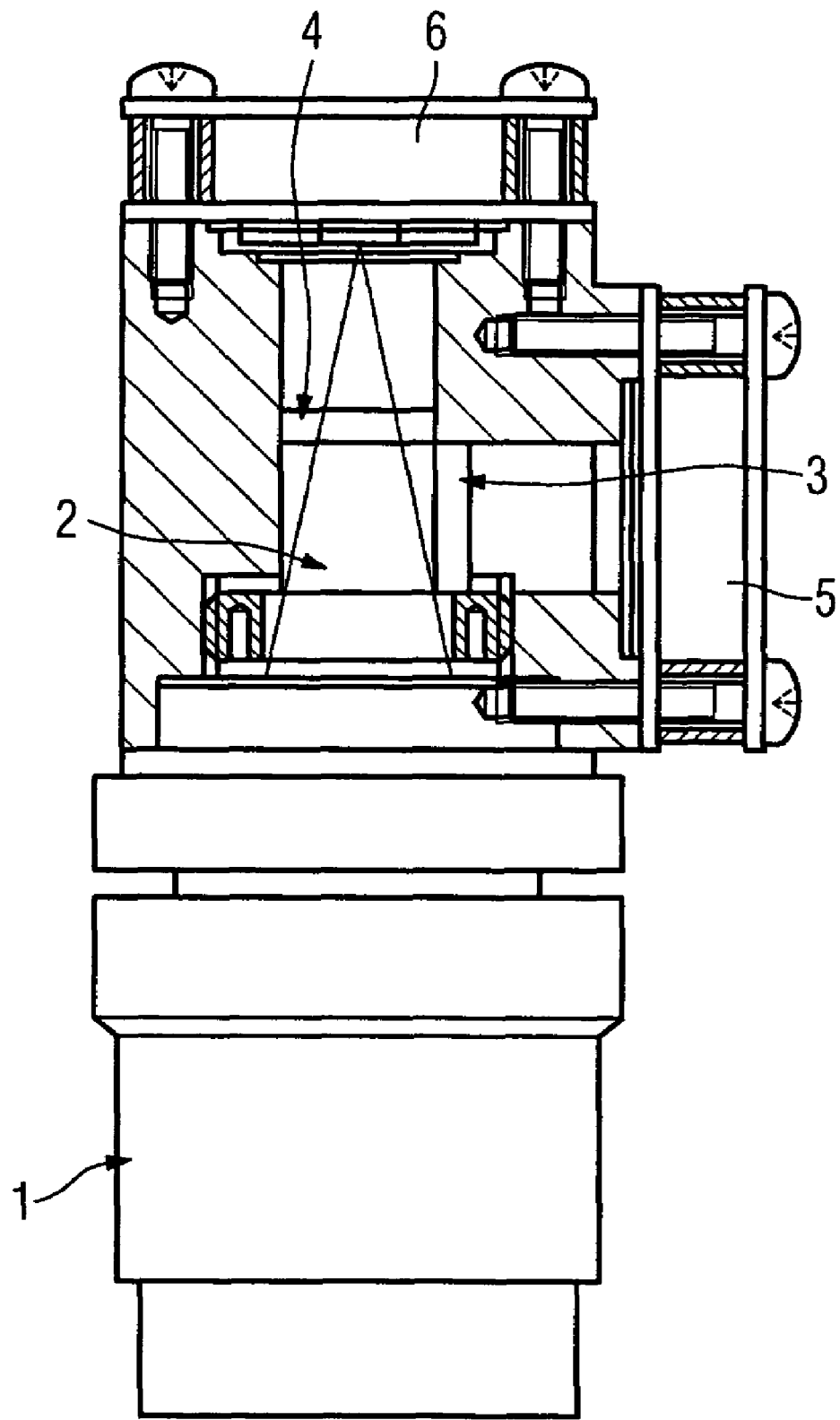
FIG. 1 shows an image acquisition device.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a sectional schematic of an image acquisition device suitable for carrying out the method according to an embodiment of the invention. A beam splitter 2 is arranged downstream of an objective 1 in the beam path. Reference numeral 3 denotes a first filter that is opaque, for example, to wavelengths in the UV region. Reference numeral 4 denotes a second filter that is, for example, opaque to wavelengths of less than 750 nm.

A first camera 5 for acquiring native tissue images reproducing a tissue surface is arranged downstream of the first filter 3 in the beam path. A second camera 6, arranged downstream of the second filter 4 in the beam path, serves the purpose of recording fluorescent images generated by fluorescent light. The first camera 5 or the second camera 6 can, in particular, be CCD cameras that expediently have a particularly high sensitivity to the wavelength regions respectively to be recorded.

Figure 2:
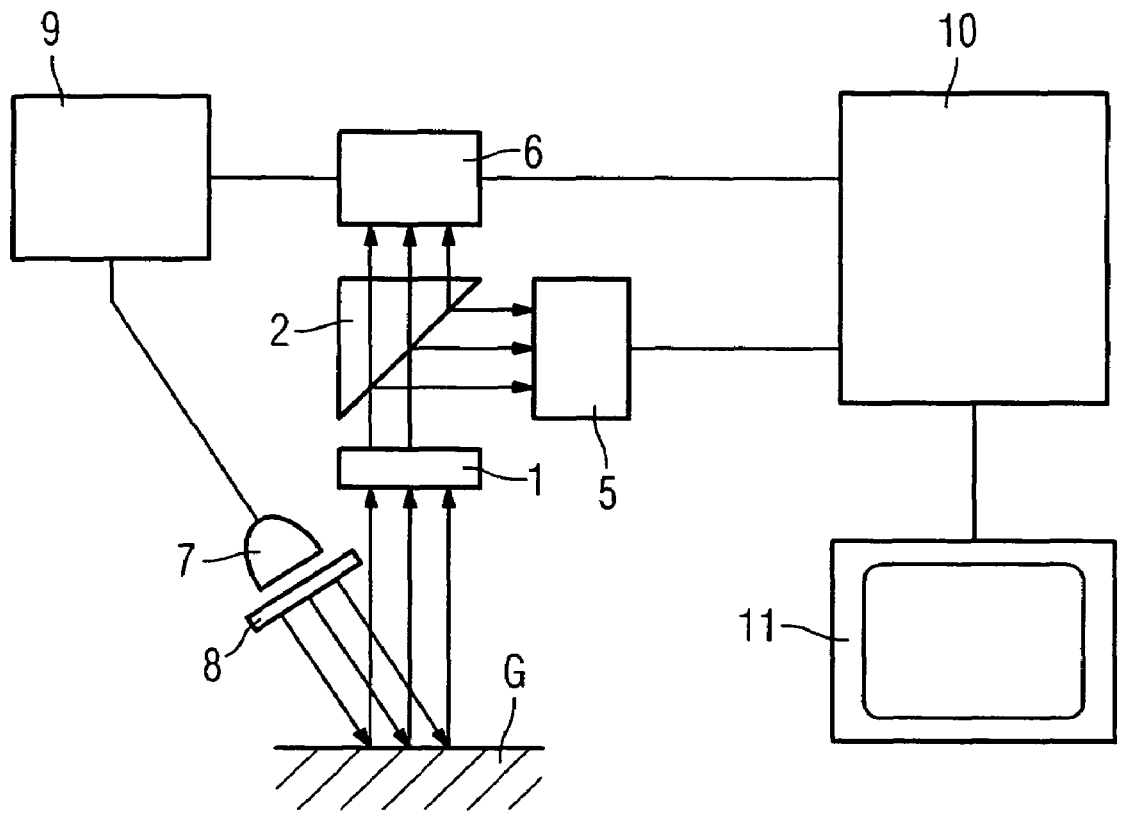
FIG. 2 shows a schematic of the essential components of an apparatus.

FIG. 2 is a schematic of the essential components of an apparatus according to an embodiment of the invention.

An exciting light source 7 can include, for example, a multiplicity of LEDs (not shown here) for generating an exciting light with a wavelength in the region of at least 700 nm, for example. Arranged downstream of the exciting light source 7 is a third filter 8, that is opaque to light with a wavelength of less than 700 nm, for example. A tissue is denoted by the reference symbol G.

The exciting light source 7 and the second camera 6 are connected to a control unit 9. It can also be the case that the first camera 5 is connected to the control unit 9. The first camera 5 and the second camera 6 are connected to a computer 10 that is, in turn, connected to a monitor 11 for displaying the generated images. Of course, it can also be that the control unit 9 is a constituent of the computer 10.

The functioning of the apparatus will now be explained in more detail in conjunction with FIG. 3.

Figure 3:
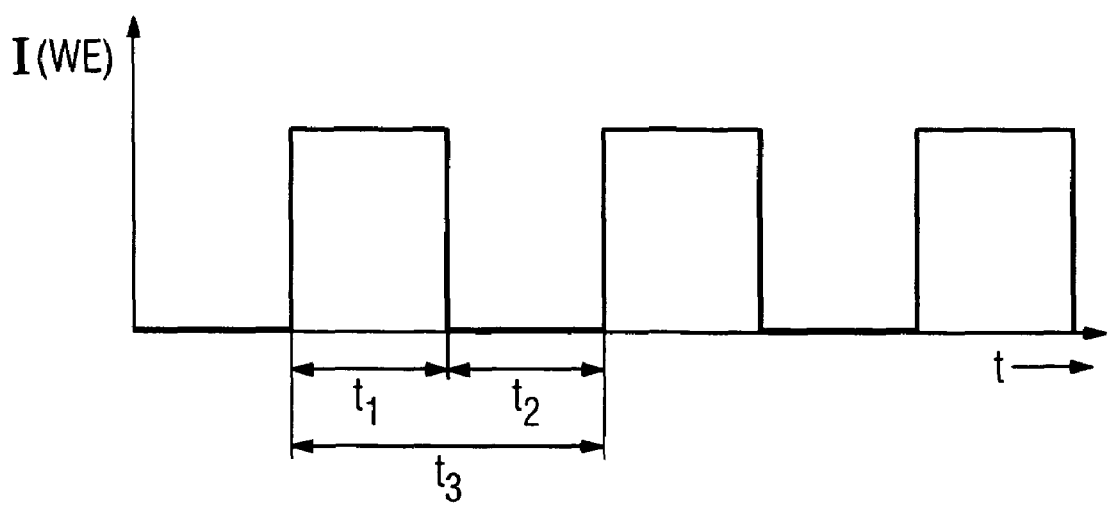
FIG. 3 shows the clock frequency for driving an exciting light source.

The control unit 9 generates the clock signal shown in FIG. 3. The clock signal can be a rectangular signal with a frequency of 40 Hz, for example. The exciting light source 7 is switched on and off in a fashion agreeing with the clock signal. The illumination and dark phases resulting thereby are denoted in FIG. 3 by the reference symbols $t_1$ and $t_2$. The first camera 5 can be switched on and off exactly in phase opposition. That is to say, the first camera 5 for recording the native tissue image can be switched on only during the dark phases $t_2$. To this end, the first camera 5 can be switched on and off in phase opposition directly by the control unit 9 via a control line that may be provided. However, it is also possible that the first camera 5 comprises a device with the aid of which the first camera 5 is switched on and off in phase opposition as a function of the light signal generated by the exciting light source 7. Furthermore, the second camera 6 can be driven with the aid of the control unit 9 such that first fluorescent images recorded during the illumination phases $t_1$, and second fluorescent images recorded during the dark phases $t_2$ are acquired separately by the computer 10.

Using a conventional image processing program, it is possible for a corrected first fluorescent image to be produced, for example, from two consecutively acquired first and second fluorescent images by subtracting the second fluorescent image from the first fluorescent image. Using conventional methods, a native tissue image recorded, for example, simultaneously with the second fluorescent image with the aid of the first camera 5 can likewise be superimposed on the first fluorescent image, the corrected first fluorescent image being displayed with a false color. The overall image thus generated indicates without the influence of interference signals exactly those regions in the tissue in which a fluorescent dye is enriched. This enables, for example, a tumor to be exactly distinguished from a healthy tissue.

The display frequency of, for example, 20 Hz assigned to the time interval denoted in FIG. 3 by $t_3$ can be used to display the overall image. Such a display frequency is sufficient for the purpose of the apparatus according to at least one embodiment of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for displaying a tissue containing a fluorescent dye, at least in sections, comprising:
    illuminating the tissue with a first light for exciting the fluorescent dye and includes a clock frequency given by a periodic sequence of illumination phases and dark phases;
    separately acquiring first fluorescent images generated during the illumination phases by excitation of the fluorescent dye, and second fluorescent images generated during the dark phases by an illumination of the tissue with a second light;
    correcting the first fluorescent images by subtracting second fluorescent images corresponding thereto; and
    generating overall images by superimposing on the corrected first fluorescent images corresponding native tissue images which reproduce a tissue surface, wherein a number of second fluorescent images are acquired in a fashion following one another temporally during the dark phase, and
    wherein, for the purpose of producing a second fluorescent image, at least one late fluorescent image acquired during a prescribed late time interval of the dark phase is subtracted from at least one early fluorescent image acquired in relation to a prescribed early time interval.

2. The method as claimed in claim 1, wherein the overall image is reproduced with a display frequency.

3. The method as claimed in claim 2, wherein the clock frequency is an integral multiple of the display frequency.

4. The method as claimed in claim 2, wherein the display frequency is 10 to 60 Hz.

5. The method as claimed in claim 2, wherein the clock frequency is twice the display frequency.

6. The method as claimed in claim 2, wherein the display frequency is 20 Hz.

7. The method as claimed in claim 1, wherein the first fluorescent image is displayed in the overall image by way of a false color.

8. The method as claimed in claim 1, wherein infrared light is used as first light.

9. The method as claimed in claim 1, wherein an infrared light of a frequency of more than 700 nm in a near infrared region, which is an infrared light of a wavelength of more than 750 nm, is used as the first light.

10. An apparatus for displaying a tissue containing a fluorescent dye, at least in sections, comprising:
    an illumination device to illuminate the tissue with a first light for exciting the fluorescent dye and includes a clock frequency given by a periodic sequence of illumination phases and dark phases;
    an acquisition device to separately acquire first fluorescent images generated during the illumination phases by the excitation of the fluorescent dye, and second fluorescent images generated during the dark phases by an illumination of the tissue with a second light;
    a correction device to correct the first fluorescent images by subtracting second fluorescent images corresponding thereto; and
    an image generating device to generate overall images by superimposing the corrected first fluorescent images with corresponding native tissue images which reproduce a tissue surface, wherein a number of second fluorescent images can be acquired via the acquisition device in a fashion following one another temporally during the dark phase, and
    wherein, in order to produce a second fluorescent image, a further correction device is provided to subtract at least one late fluorescent image acquired during a prescribed late time interval of the dark phase from at least one early fluorescent image acquired in relation to a prescribed early time interval.

11. The apparatus as claimed in claim 10, further comprising: a device to generate a display frequency for reproducing the overall image.

12. The apparatus as claimed in claim 11, wherein the excitation frequency is an integral multiple of the display frequency.

13. The apparatus as claimed in claim 10, wherein the excitation frequency is 10 to 60 Hz.

14. The apparatus as claimed in claim 10, further comprising:
    a device to display the first fluorescent image in the overall image by means of a false color.

15. The apparatus as claimed in claim 10, wherein the first light is infrared light.

* * * * *